(12) United States Patent
Yokoyama (10) Patent No.: US 8,522,603 B2
(45) Date of Patent: Sep. 3, 2013

(54) METHOD FOR ANALYSIS OF SACCHARIDES

(75) Inventor: Tetsuo Yokoyama, Hyogo (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 650 days.

(21) Appl. No.: 12/722,648

(22) Filed: Mar. 12, 2010

(65) Prior Publication Data

US 2010/0229634 A1    Sep. 16, 2010

(30) Foreign Application Priority Data

Mar. 13, 2009    (JP) .................................. 2009-060917

(51) Int. Cl.
*G01N 30/04*    (2006.01)
*G01N 21/64*    (2006.01)
*G01N 33/00*    (2006.01)

(52) U.S. Cl.
USPC ... 73/61.55; 73/61.52; 210/198.2; 422/82.08; 436/94; 436/95; 436/161; 436/172

(58) Field of Classification Search
USPC .................... 73/61.52, 61.55, 61.56; 436/94, 436/95, 161, 171, 172; 210/198.2; 422/82.08
See application file for complete search history.

(56) References Cited

U.S. PATENT DOCUMENTS 4,278,438 A * 7/1981 Walraven ........................ 436/94
4,486,308 A * 12/1984 Hirai et al. .................. 210/502.1
5,334,704 A * 8/1994 Tsunoo et al. ................ 530/371
7,947,507 B2 * 5/2011 Venkataraman et al. ..... 436/106
2010/0035328 A1    2/2010 Oki et al.

FOREIGN PATENT DOCUMENTS

| JP | 54-107399 A | * | 8/1979 |
| JP | 55-70739 A | * | 5/1980 |
| JP | 57-116256 A | * | 7/1982 |
| JP | 58-216953 A |   | 12/1983 |
| JP | 61-25059 A |   | 2/1986 |
| JP | 2-201261 A | * | 8/1990 |
| JP | 2006-184131 A |   | 7/2006 |

OTHER PUBLICATIONS

Mrochek, J.E. et al., "Liquid-Chromatographic Analysis for Neutral Carbohydrates in Serum Glycoproteins", Clinical Chemistry, vol. 21, No. 9, 1975, pp. 1314-1322.*
European Search Report of EP 10 15 6313 (May 17, 2010).

(Continued)

*Primary Examiner* — Daniel Larkin
(74) *Attorney, Agent, or Firm* — Millen, White, Zelano & Branigan, P.C.

(57) ABSTRACT

Disclosed is an improved post-column fluorimetric determination-boric acid complex anion exchange method which allows analysis of mannose-6-phosphate. The disclosed method is a method for separation analysis of reducing sugars using column chromatography, comprising loading a sample onto an anion exchange column, washing the column by allowing to flow a sufficient volume of a first mobile phase consisting of an aqueous solution of a predetermined concentration of boric acid containing a predetermined concentration of a water-soluble inorganic salt through the column, supplying a second mobile phase with an elevated concentration of the salt to elute the reducing sugars, adding to the eluate a basic amino acid, heating, and continuously measuring and recording the intensity of fluorescent light emitted under irradiation with excitation light.

16 Claims, 7 Drawing Sheets

(56) References Cited

OTHER PUBLICATIONS

S. Sawada et al., "Determination of Sugar Phosphates and Nucleotides Related to Photosynthesis Metabolism by High-Performance Anion-Exchange Liquid Chromatography with Fluorometric and Ultraviolet Detection," Analytical Biochemistry, vol. 314 (2003) pp. 63-69.

G. K. Ward et al., "Molal Volume of Aqueous Boric Acid-Sodium Chloride Solutions," Journal of Solution Chemistry, vol. 3, No. 6 (1974) pp. 431-444.

L. Verhaar et al., "The Analysis of Sugars and Sugar Alcohols by Ion-Exchange Chromatography," Carbohydrate Research, vol. 59 (1977) pp. 1-10.

K. Jinno et al., "Separation of Saccharides on Cross-Linked Chitosan Beads with Microcolumn Liquid Chromatograhpy," J. Microcolumn Separations, vol. 1, No. 4 (1989) pp. 195-199.

H. Bauer et al., "Ionenaustausch-Chromatographie von Kohlenhydraten, Chromatographia," vol. 9, No. 9 (Sep. 1976) pp. 433-438.

H. Mikami et al., "Post-Column Fluorometric Detection of Reducing Sugars in High Performance Liquid Chromatography Using Arginine," Bunseki Kagaku, vol. 32 (1983) pp. E207-E210.

J. Bielicki et al., "Recombinant Human Iduronate-2-Sulphatase : Correction of Mucopolysaccharidosis-Type II Fibroblasts and Characterization of the Purified Enzyme," Biochem. J., vol. 289 (1993) pp. 241-246.

* cited by examiner

METHOD FOR ANALYSIS OF SACCHARIDES

FIELD OF THE INVENTION

The present invention relates to a method for analysis of saccharides, in particular a method for analysis of reducing sugars and mannose-6-phosphate employing a post-column fluorometric determination-boric acid complex anion exchange method.

BACKGROUND OF THE INVENTION

A method for analysis of reducing sugars is known by subjecting a sample to liquid chromatography using water as the mobile phase, adding to the eluate thus obtained an aqueous solution of boric acid containing a basic amino acid such as arginine, allowing a reaction to proceed under heating, then cooling the reaction mixture solution and irradiate it with excitation light and measuring the intensity of fluorescence or absorbance (Patent Document 1). The apparatus used there is made up of a liquid chromatograph with an extended flow path, to which is connected a supply channel for a boric acid solution containing a basic amino acid, and to which flow path are further attached a heating device, a cooling device, an excitation light irradiator, and a device measuring fluorescence intensity. According to this method, a supply channel is indispensable to add a boric acid solution containing a basic amino acid to the eluate from the chromatograph to allow a reaction to take place.

Further, as an improved type of the above method, a method is known in which a sample is applied to liquid chromatography using a mobile phase containing a basic amino acid such as arginine and boric acid, which are the reagents for the reaction, and is eluted, and the eluate thus obtained is heated to let the reagents and saccharides react (heat reaction) and then cooled, and this reaction mixture solution then is measured for intensity of fluorescence emitted under irradiation with excitation light, or for absorbance (Patent Document 2). In this method, as an aqueous solution of boric acid containing a basic amino acid is employed as the mobile phase for liquid chromatography, there is no need for providing a supply channel for addition of an aqueous solution of boric acid containing a basic amino acid in order for allowing a reaction to proceed. The above methods for analysis of reducing sugars are called post-column fluorometric determination-boric acid complex anion exchange method.

The methods for analysis of reducing sugars mentioned above both utilize in detection the production of a strong fluorogenic derivative through the heat reaction of reducing sugars with a basic amino acid, such as arginine, in the presence of boric acid (Non-patent Document 1). This strong fluorogenic derivatives is brown-colored melanoidine formed by the heat reaction (Maillard reaction) of reducing sugars and a basic amino acid, i.e., an amino compound, and it emits light at the wavelength of 430 nm when irradiated with excitation light at the wavelength of 320 nm. These method for analysis of reducing sugars utilize that reducing sugars have a property of readily binding to boric acid to form an anionic complex ion, and that this anionic complex ion is retained in anion exchanger column chromatography.

In the post-column fluorometric determination-boric acid complex anion exchange method, an aqueous solution (pH 7-10) is employed which contains a basic amino acid at a concentration of 0.01-5% and boric acid at a concentration of 0.05-0.5 M. Those amino acids which are employed there are arginine, lysine, histidine, and the like. Recently, it is further known to perform analysis of sugars employing as a mobile phase for liquid chromatography a gradient formed between a 0.1 M borate buffer and a 0.4 M borate buffer (Patent Documents 3, 4).

In the post-column fluorometric determination-boric acid complex anion exchange method, elution of a sample by liquid chromatography is carried out at temperatures of from room temperature to 70° C., and the heat reaction (Maillard reaction) is let proceed at 140-180° C. Since elution and reaction are performed at such high temperatures and at high boric acid concentrations, boric acid contained in the mobile phase sometimes precipitates and clog the tubing. Once the tubing is clogged, the analysis can no longer be continued, and it therefore must be done over again after a costly and troublesome job like exchanging and washing the tubing. This is an unsolved major problem with the post-column fluorometric determination-boric acid complex anion exchange method.

Further, the sugars which can be analyzed using the post-column fluorometric determination-boric acid complex anion exchange method include monosaccharides such as glucose, mannose, galactose, fructose, and rhamnose; oligosaccharides such as maltose and maltotriose; amino sugars such as glucosamine, galactosamine; and uronic acid such as glucuronic acid An example of analytes of this method is sugar chains of glycoproteins. Those reducing sugars which form sugar chains of glycoproteins include neutral sugars such as mannose, galactose and fucose; amino sugars such as galactosamine. Sugar chains sometimes contain mannose-6-phosphate (M6P), in which mannose is modified with one molecule of phosphoric acid.

M6P contained in sugar chains of glycoproteins has an important function to promote uptake of those proteins when they are being taken up into cells, through its binding to a mannose-6-phosphate receptor on the cell membrane. Lysosomal enzymes, such as iduronate-2-sulfatase (I2S) localized in lysosomes, are known as proteins containing M6P in their sugar chains (Non-patent document 2). Some lysosomal enzymes are produced by recombinant technology and used as therapeutic drugs for patients who hereditarily lack those enzymes. They are, for example, $\alpha$-galactosidase A and glucocerebrosidase. Because lysosomal enzymes are enzymes which function within the cells, for those lysosomal enzymes administered to a patient in some manner, such as by intravenous injection, to exhibit pharmacological effects, they must be taken up into the cells of the patient, and for this to happen, it is necessary that the sugar chains of the lysosomal enzymes contain M6P. Thus, it is particularly important to analyze M6P when sugars forming the sugar chains of such enzymes are to be analyzed. While the post-column fluorometric determination-boric acid complex anion exchange method can be used as an analytical technique for a variety of sugars, no technique has been established to analyze M6P using this method.

PRIOR ART DOCUMENTS

Patent Documents

[Patent Document 1] Japanese Patent Application Publication No. S58-216953
[Patent Document 2] Japanese Patent Application Publication No. S61-25059
[Patent Document 3] Japanese Patent Application Publication No, 2006-184131

[Patent Document 4] Japanese Patent Application Publication No. 2008-425550

Non-Patent Document

[Non-patent Document 1] Mikami H. et. Al., Bunseki Kagaku (1983) 32, E207
[Non-patent Document 2] Bielicki J. et. Al., Biochem J. (1993) 289, 241-246

SUMMARY OF THE INVENTION

Problem to be Solved by the Invention

Against the background mentioned above, an objective of the present invention is to modulate the retention power of the anion exchanger resin, which is employed in the post-column fluorometric determination-boric acid complex anion exchange method, toward anionic complex ions, thereby enabling measurement of M6P, and simultaneously, to enhance its ability to analyze neutral sugars such as mannose, fucose, and glucose.

Further, another objective of the present invention is to substantially solve the problem of the above method that clogging of the tubing occurs due to the precipitation of boric acid contained in the mobile phase.

Means to Solve the Problem

In a study for solving the above problem, the present inventor attempted to use an aqueous solution of boric acid and a water-soluble neutral salt like sodium chloride as a mobile phase in the post-column fluorometric determination-boric acid complex anion exchange method. As a result, it was found that in such a mobile phase, the retention power of the anion exchange resin toward anionic complex ion can be modulated by means of the concentration of the water-soluble neutral salt, and surprisingly that it enables analysis of M6P, which could not be analyzed by a conventional method. Further, it was also found that the ability of analyzing neutral reducing sugars such as mannose, fucose, and glucose can be markedly improved as compared with conventional methods. Furthermore, it was also found that addition of sodium chloride enables one to reduce the concentration of boric acid in the mobile phase, and thereby substantially solve the problem of the post-column fluorometric determination-boric acid complex anion exchange method that the tubing is clogged due to precipitated boric acid.

The present invention was completed on the basis of these discoveries.

Thus the present invention provides the following aspects

Aspect 1. A method for separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid containing at least a predetermined concentration of a water-soluble inorganic salt through the column;
supplying to the column continuously at a predetermined flow rate a second mobile phase containing the salt at an elevated concentration compared with the first mobile phase to eluate reducing sugars;
leading the eluate from the column continuously to a flow path;
continuously adding at least one basic amino acid at a predetermined rate to the eluate at a predetermined position of the flow path to make a mixture solution which continuously flows through the flow paths;
heating the mixture solution by letting the mixture solution flow through a heating zone at a predetermined temperature of the flow path over a predetermined length of times; and
continuously measuring and recording the intensity of fluorescent light emitted from the mixture solution while continuously irradiating the mixture solution thus heated and flowing through the flow path with excitation light at a predetermined position of the flow path.

Aspect 2. A method for separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid containing at least a predetermined concentration of a basic amino acid and a predetermined concentration of a water-soluble inorganic salt through the column;
supplying to the column continuously at a predetermined flow rate a second mobile phase containing the salt at an elevated concentration compared with the first mobile phase to eluate reducing sugars;
leading the eluate from the column continuously to a flow path;
heating the eluate solution by letting the eluate flow through a heating zone of the flow path at a predetermined temperature over a predetermined length of time; and
continuously measuring and recording the intensity of fluorescent light emitted from the eluate while continuously irradiating the eluate thus heated and flowing through the flow path with excitation light at a predetermined position of the flow path.

Aspect 3. The method for separation analysis according to Aspect 1 or Aspect 2 above, wherein, in the first mobile phase, the concentration of boric acid is 50-150 mM and the concentration of the water-soluble inorganic salt is 10-30 mM.

Aspect 4. The method for separation analysis according to Aspect 3 above, wherein the concentration of boric acid in the first and the second mobile phases is 75-125 mM.

Aspect 5. The method for separation analysis according to one of Aspects 1 to 4 above, wherein the pH of the first and the second mobile phases is 7.5-9.5.

Aspect 6. The method for separation analysis according to one of Aspects 1 to 5 above, wherein the water-soluble inorganic salt is sodium chloride.

Aspect 7. The method for separation analysis according to one of Aspects 1 to 6 above, wherein separation of reducing sugars is performed with the column heated at a temperature not exceeding 70° C.

Aspect 8. The method for separation analysis according to one of Aspects 1 to 7 above, wherein the basic amino acid is either added so that the concentration thereof reaches 0.1-2 w/v % in the mixture solution or included in the first and second mobile phases so that the concentration there of reaches 0.1-2 w/v % in the mobile phases.

Aspect 9. The method for separation analysis according to one of Aspects 1 to 8 above, wherein the basic amino acid is selected from the group consisting of arginine, lysine and histidine.

Aspect 10. The method for separation analysis according to one of Aspects 1 to 9 above, wherein the temperature of the heating zone at a predetermined temperature is 140-180° C.

Aspect 11. The method for separation analysis according to one of Aspects 1 to 10 above, wherein the concentration of the salt in the second mobile phase is increased at least up to 200 mM.

Aspect 12. The method for separation analysis according to one of Aspects 1 to 11 above, wherein the reducing sugars include neutral sugars.

Aspect 13. The method for separation analysis according to one of Aspects 1 to 12 above, wherein the reducing sugars include mannose, glucose or fucose.

Aspect 14. The method for separation analysis according to one of Aspects 1 to 13 above, wherein the reducing sugars include mannose-6-phosphate.

Aspect 15. An aqueous solution for use as the first mobile phase in one of Aspects 1 to 14 above, wherein the aqueous solution contains 50-150 mM boric acid and 10-30 mM sodium chloride.

Aspect 16. An aqueous solution for use to prepare the second mobile phase by mixing with the first mobile phase in one of Aspects 1 to 14 above, wherein the aqueous solution contains 50-150 mM boric acid and 200-250 mM sodium chloride.

Aspect 17. A solid composition for use to prepare the aqueous solution of Aspect 15 above by dissolving the same in water, wherein the solid composition comprises boric acid and sodium chloride at a molar ratio of 1:0.1 to 1:0.5.

Aspect 18. A solid composition for use to prepare the aqueous solution of Aspect 16 above by dissolving the same in water, wherein the solid composition comprises boric acid and sodium chloride at a molar ratio of 1:1.5 to 1:2.5.

Effect of the Invention

In the post-column fluorometric determination-boric acid complex anion exchange method, the present invention enables analysis of M6P, and enhances the method's ability of analyzing reducing sugars. Furthermore, as the present invention employs lower concentrations of boric acid compared with a conventional post-column fluorometric determination-boric acid complex anion exchange method, clogging of the tubing, a problem with the conventional method, is substantially eliminated.

BRIEF DESCRIPTION OF THE FIGURES

FIG. 2-1 shows a chromatogram showing the result of analysis of a neutral reducing sugars mixture standard solution according to the novel method.

FIG. 2-2 shows a chromatogram showing the result of analysis of a neutral reducing sugars mixture standard solution according to a conventional method.

FIG. 3-1 shows a chromatogram showing the result of analysis of an M6P standard solution according to the novel method.

FIG. 3-2 shows a chromatogram showing the result of analysis of an M6P standard solution according to a conventional method.

FIG. 4-1 shows a chromatogram showing the result of analysis of a mixture of a neutral sugars mixture standard solution and an M6P standard solution according to the novel method.

FIG. 4-2 shows a chromatogram showing the result of analysis of a mixture of a neutral sugars mixture standard solution and an M6P standard solution according to a conventional method.

DETAILED DESCRIPTION OF THE INVENTION

In the present invention, the term "aqueous solution of boric acid" includes such a solution which contains a small amount of a base as a pH adjusting agent, such as sodium hydroxide (or sodium borate) for adjusting the pH as desired.

In the present invention, the term "concentration of boric acid", when used in connection with an aqueous solution of boric acid, means a calculated concentration of boric acid ($H_3BO_3$) which could be derived by replacing boron in the aqueous solution with boric acid. Therefore, the term also includes boric acid added in the form of a salt (like sodium borate).

In the present invention, in order to elevate the salt concentration in the second mobile phase, another boric acid solution containing the salt at an elevated concentration, for example, may be added to the first mobile phase while increasing the mixing ratio of the former. In doing this, though the mixing ratio may be increased either continuously or intermittently, it is preferably increased continuously, and most preferably increased in a linear fashion (i.e., continuously and at a constant flow rate). The elevation of the salt concentration in the second mobile phase may be done until the analyte, i.e., reducing sugars, have been eluted. It generally is enough to elevate the salt concentration until it reaches around 200 mM, but it is also allowed to further elevate the salt concentration until it reaches 250 mM.

In the present invention, though there is no particular restriction as to what salt is to be contained in the first mobile phase as far as the salt is a water-soluble inorganic salt (but excluding borate), a neutral salt, which gives a neutral pH when dissolved in water, is preferred, and sodium chloride and potassium chloride are particularly preferred.

In the present invention, the concentration of boric acid in the mobile phases is preferably 50-150 mM, more preferably 75-125 mM, and most preferably about 100 mM, though there is no restriction as far as it allows analysis of sugars to be carried out, especially neutral reducing sugars or M6P according to the purpose.

In the present invention, the pH of the mobile phases is preferably 7.5-9.5, and most preferably about 9.

As an anion exchanger resin employed in the anion exchanger column chromatography in the present invention, a strong anion exchanger resin is preferably used, though either a weak anion exchanger resin or a strong anion exchanger resin may be used. Elution from an anion exchanger column may be carried out at room temperature, but preferably it is carried out while heating the column. When heating, however, the temperature should not to exceed about 70° C., and preferably it is about 65° C.

The basic amino acids used in the present invention, though not particularly restricted, are preferably arginine, lysine or histidine, and arginine is particularly preferred. While one of basic amino acids may be employed alone, two or more basic amino acids may also be employed in a mixture. Addition of a basic amino acid is done by injecting a solution containing the same into the eluate flowing out of the column and through the flow path. The speed of injection of a basic amino acid may be set as desired insofar as the speed is kept constant during a single round of analysis. In general, such injection may be made so that the concentration (final concentration) after mixing with the eluate from the column in the flow path reaches 0.1-2 w/v % preferably 0.5-1.8 w/v %, and more preferably 1.0-1.5 w/v %. Addition of a basic amino acid is preferably performed, for example, by injection in the form of an aqueous solution of boric acid containing the basic amino acid. In such a case, though the concentration of boric acid may be adjusted to be equal to the concentration of boric acid in the mobile phases, there will be no problem if it differs to some degree. Alternatively, addition of a basic amino acid may be done by dissolving in advance a basic amino acid at a predetermined concentration in the aqueous solutions used as mobile phases. The concentration of amino acid may be adjusted to 0.1-2 w/v %, preferably 0.5-1.8 w/v %, and more preferably 1.0-1.5 w/v %. In this method, as an aqueous solution of boric acid containing a basic amino acid is employed as the mobile phase for liquid chromatography, there is no need for providing a supply channel for addition of an aqueous solution of boric acid containing a basic amino acid in order for allowing a reaction to proceed.

In the present invention, the temperature at which the eluate is reacted with a basic amino acid by heating (heat reaction) may be 140-180° C., and preferably about 150° C. This reaction is Maillard reaction, in which the reducing group of the reducing sugars and basic amino acid react to form a brown pigment (melanoidine).

In the present invention, measurement of the intensity of fluorescent light is performed for fluorescent light at the wavelength of about 430 nm emitted by irradiating the reaction mixture solution after heat reaction with ultraviolet light at the wavelength of about 320 nm as excitation light. In performing this, it is preferred that the reaction mixture solution is cooled down before measurement of the intensity of fluorescent light around room temperature, using a cooling device in order to prevent generation of noises.

The sugars that can be analyzed according to the present invention are those reducing sugars that undergo Maillard reaction with basic amino acids. Examples include monosaccharides such as glucose, mannose, galactose, fructose, rhamnose and the like; oligosaccharides such as maltose, maltotriose and the like; amino sugars such as glucosamine, galactosamine and the like, uronic acid such as glucuronic acid, and phosphated saccharides, among which neutral sugars such as mannose, glucose and fucose, and phosphated sugars such as mannose-6-phosphate.

Further, in order for enhancing easiness of the operation in performing analysis, it would be advantageous that the mobile phases employed in the present invention is provided beforehand as reagents. Such reagents may take the form of an aqueous solution or a solid composition (powder, granules) which will form a mobile phase when dissolved in purified water. In the case of an aqueous solution, a reagent to be used as the first mobile phase contains boric acid preferably at 50-150 mM, more preferably at 75-125 mM, for example about 100 mM, and 10-30 mM sodium chloride, at pH 7.5-9.5. PH may be adjusted, for example, by addition of sodium hydroxide, or by replacing part of boric acid with sodium borate (e.g., borax), in either case of which the composition of the solutions thus prepared is identical.

The reagent in the form of an aqueous solution to be added to and mixed with the first mobile phase to prepare the second mobile phase may, for example, an aqueous solution containing boric acid preferably at 50-150 mM, more preferably at 75-125 mM, e.g., about 100 mM and sodium chloride preferably at 200-250 mM, e.g., about 200 mM, at pH 7.5-9.5.

In the case of a reagent in the form of a solid composition which is to be dissolved in purified water to form the first mobile phase, the composition is a blend of boric acid with sodium chloride at such a ratio that, when dissolved in water, can give the concentration of boric acid of 50-150 mM, 75-125 mM, e.g., about 100 mM, and the concentration of sodium chloride of 10-30 mM. Therefore, a solid composition may comprise, for example, boric acid and sodium chloride at a molar ratio of 1:0.1 to 1:0.5, in which the pH of the aqueous solution to be prepared can be adjusted in advance by inclusion of a proper amount of sodium borate in place of part of boric acid.

In the above case, preparation of a blend so that it, when dissolved in a predetermined amount of water, gives such pH values, may be performed, for example, by preparing a small volume of the intended aqueous solution in advance to determine the amount of boric acid and sodium borate (borax or the like) needed to make the pH within the predetermined range, and thereafter, based on the amount thus determined, blending a proper amount of boric acid and sodium borate (borax or the like) in accordance with the volume of the solution to be prepared. Besides, in the case where the pH of the aqueous solution was adjusted by addition of sodium hydroxide, the amount of sodium borate required for pH adjustment using sodium borate, instead of sodium hydroxide, is the amount of sodium borate corresponding to the number of moles of Na ion which is equal to the number of moles of the Na ion from the sodium hydroxide which was required. Further, the amount of boric acid employed is reduced by the amount which corresponds to the number of moles of boric acid which comes from the sodium borate added.

The solid composition as a reagent which is to be dissolved in water to prepare an aqueous solution containing a high concentration of sodium chloride which aqueous solution then is to be added to the first mobile phase to prepare the second mobile phase, is a blend prepared so that it, when dissolved in water, can give the concentration of boric acid preferably at 50-150 mM, more preferably at 75-125 mM, e.g., at about 100 mM and the concentration of sodium chloride at 200-250 mM, and pH at 7.5-9.5. Therefore, a solid composition may comprise boric acid and sodium chloride at a molar ratio, for example, of 1:1.5 to 1:2.5.

EXAMPLES

Though the present invention will be described in further detail below with reference to examples, it is not intended that the present invention be limited to those examples.

[Preparation of Standard Solutions]

Thirty mg of D(+)-mannose, 10 mg of L(−)-fucose, and 30 mg of D(+)-galactose were dissolved in purified water to make 100-mL. To 18 mL of this solution was added purified water to make 50 mL, and was used as the neutral reducing sugar mixture standard solution. Twenty mg of sodium mannose-6-phosphate was dissolved in water to make 100 mL and this was used as the M6P standard solution. The M6P standard stock solution was frozen stored in 1 mL aliquots at −20° C., which was thawed before use, and diluted twofold with purified water and used as the M6P standard solution.

[Preparation of Solutions for Mobile Phases (for Novel Method)]

To purified water was added 6.2 g of boric acid and allowed to dissolve, and after adjusting the pH of this solution to 9.0 with 2N sodium hydroxide, purified water was added to make the total volume of 1000 mL, which then was suction-filtered through a 0.22 μm membrane filter. The solution thus obtained was designated as solution A (100 mM boric acid solution (pH 9.0)). To purified water were added 6.2 g of boric acid and 11.7 g of sodium chloride and allowed to dissolve, and after adjusting the pH of this solution to 9.0 with 2N sodium hydroxide, purified water was added to make the total volume of 1000 mL, which then was suction-filtered through a 0.22 μm membrane filter. The solution thus obtained was designated as solution B (100 mM boric acid-200 mM sodium chloride solution (pH 9.0)).

[Preparation of Solution for Mobile Phases (for Conventional Method)]

To purified water was added 6.2 g of boric acid and was allowed to dissolve, and after adjusting pH to 8.0 with 2N sodium hydroxide, purified water was added to make the total volume of 1000 mL, which then was suction-filtered through a 0.22 μm membrane filter. The solution thus obtained was designated as solution A' (100 mM boric acid solution (pH 8.0)). To purified water was added 24.8 g of boric acid and allowed to dissolve, and after adjusting pH to 9.0 with 2N sodium hydroxide, purified water was added to make the total volume of 1000 mL, which then was suction-filtered through a 0.22 μm membrane filter. The solution thus obtained was designated as solution 13' (400 mM boric acid solution (pH 9.0)).

[Preparation of Reagent Solution (Solution C) for Reaction]

To purified water were added 10 g of L-arginine and 30 g of boric acid and allowed to dissolve, and the total volume was adjusted to 1000 mL, suction-filtered through a membrane filter with the pore size of not more than 0.22 μm, and the solution, Solution C, thus obtained was used as the reagent solution for reaction.

[Analysis of Sugars by Post-Column Fluorometric Determination-Boric Acid Complex Anion Exchange Method (1)]

(1) Apparatus

Figure 1:
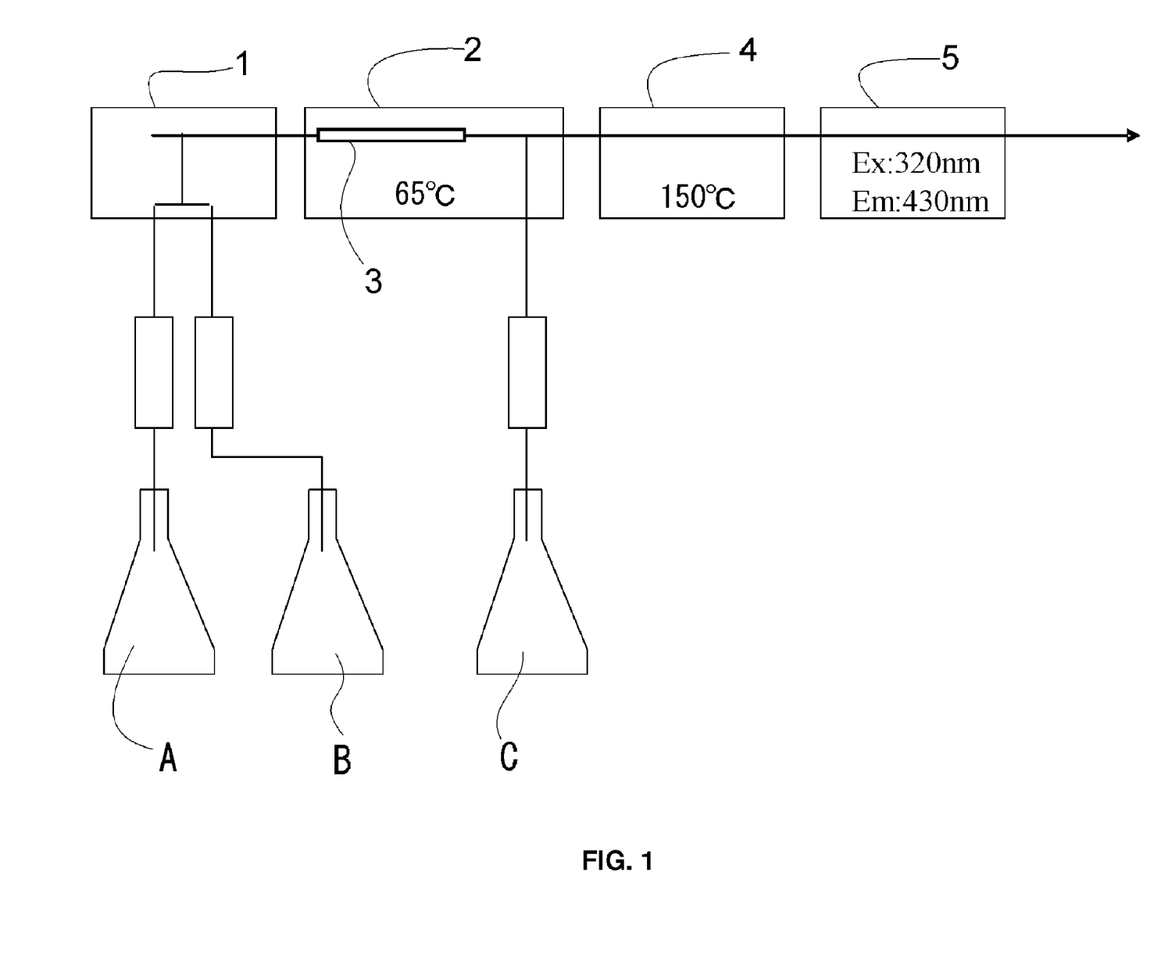
FIG. 1 shows a schematic diagram illustrating the arrangement of the apparatus and the flow paths.

An anion exchanger column, Shimpack ISA-07/S2504 (4.0 mm I.D.×250 mm)(base material: polystyrene gel, stationary phase: quaternary ammonium group) was attached to Shimazu HPLC System LC-10Avp (reducing sugar analysis system), and further, Shim-pack guard column ISA (4.0 mm I.D.×50 mm) was set as a column oven used to heat the column. A heat block (ALB-221, mftd. by Asahi Techno Glass) for heat reaction was set downstream of the outlet of the column. The column was heated in the column oven at 65° C., and the heat block was set at 150° C. A fluorescence detector system was installed downstream of the heat block, and adjusted so that it would irradiate excitation light at the wavelength of 320 nm and detect fluorescent light at the wavelength of 430 nm. The arrangement of the apparatus and the flow paths are illustrated in FIG. 1.

(2) Operation Procedures

The solutions A and B were set on the Autosampler of the reducing sugar analysis system, which then was set so that the reagent solution for reaction, Solution C, was supplied downstream of the outlet of the column (upstream of the heat block). After the column was equilibrated with the mobile phase (solution A) with which chromatography was to be started, the neutral reducing sugars mixture standard solution and the M6P standard solution or a mixture solution of these were loaded onto the column.

In the novel method, after the columns were loaded with the standard solutions of the sugars, a first mobile phase prepared by mixing solution A and solution B at a volume ratio of 90:10 (thus, containing 100 mM boric acid and 20 mM sodium chloride) was passed through the column at the flow rate of 0.3 mL/min for 35 min; then the volume ratio between solution A and solution B was changed in a linear fashion to 25:75 over 25 min at the same flow rate (thus, containing 100 mM boric acid, while sodium chloride being increased up to 150 mM), and further the volume ratio of solution B was set at 100% (thus, containing 100 mM boric acid and 200 mM sodium chloride) and the solution was passed at the same flow rate for 10 min, and then solution A and solution B were passed at a volume ratio of 90:10 (thus, containing 100 mM boric acid and 20 mM sodium chloride) as was the case of the first mobile phase. The reagent solution for reaction, Solution C, was supplied to the flow path downstream of the outlet from the column at a flow rate of 0.2 mL/min. Thus, the concentration of arginine in the reaction mixture solution was 3×0.2/(0.3+0.2)=1.2 w/v %.

The compositions and the conditions for chromatography according to the novel and conventional methods are shown in Table 1, and the ratio of solution B and solution B' in Table 2, respectively.

TABLE 1

Compositions of the Solutions and Conditions for Chromatography

|  | Novel method | Conventional method |
|---|---|---|
| Method for detection (Fluorescence) | Excitation light 320 nm, Fluorescent light 430 nm | Excitation light 320 nm, Fluorescent light 430 nm |
| Solutions A, A' | 100 mM boric acid (pH 9.0) | 100 mM boric acid (pH 8.0) |
| Solutions B, B' | 100 mM boric acid, 200 mM NaCl (pH 9.0) | 400 mM boric acid (pH 9.0) |
| Flow rate of mobile phases | 0.3 mL/min | 0.6 mL/min |
| Column Temperature | 65° C. | 65° C. |
| Reagents for reaction | 1 w/v % boric acid, 3 w/v % dl-arginine | 1 w/v % boric acid, 3 w/v % dl-arginine |
| Injection speed of reagents for reaction | 0.2 mL/min | 0.5 mL/min |
| Temperature of reaction bath | 150° C. | 150° C. |

TABLE 2

Ration of Solutions B and B'

| Novel method | | Conventional method | |
|---|---|---|---|
| Time (min) | % B | Time (min) | % B' |
| 35 | 10 | 50 | 0→100 |
| 25 | 10→75 | 20 | 100 |
| 10 | 100 | Thereafter | 0 |
| Thereafter | 10 | | |

[Analysis of the Neutral Sugars Mixture Standard Solution]

Figure 21:
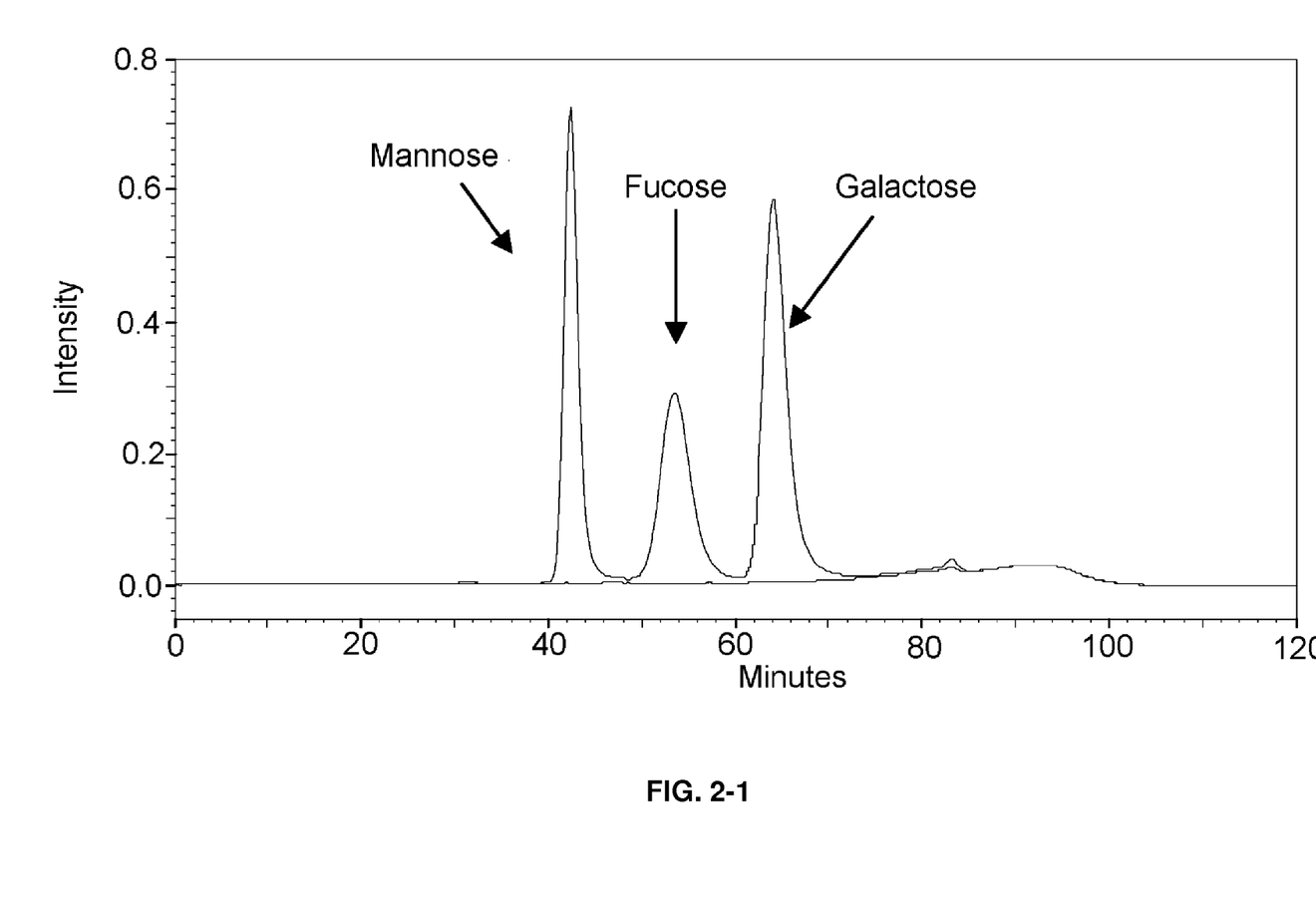
Figure 22:
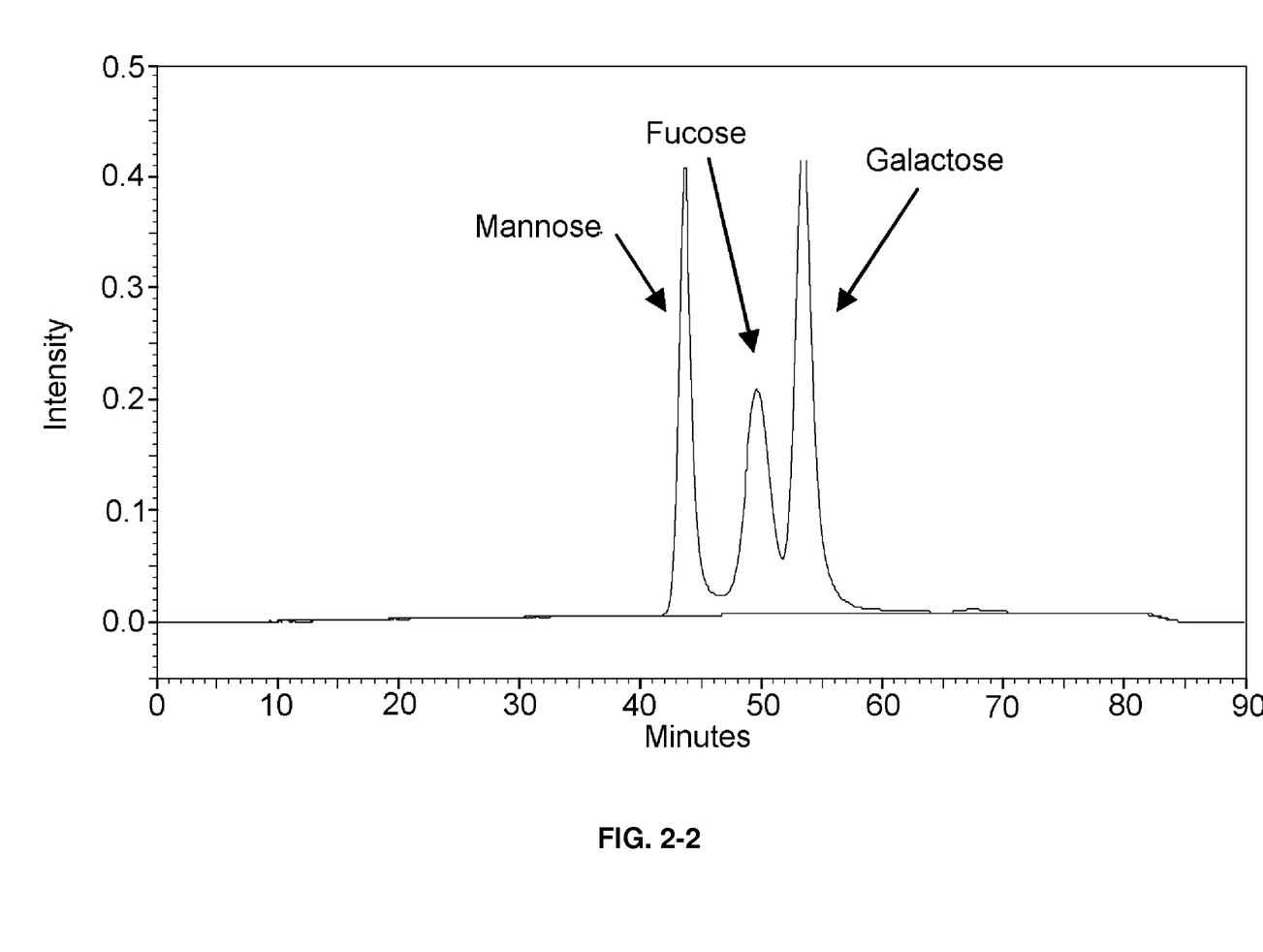

Analysis of the neutral sugars mixture standard solution according to the novel method gave completely separated peaks of fluorescence intensity ascribed to mannose, fucose and galactose were obtained (FIG. 2-1). On the other hand, analysis of the neutral sugars mixture standard solution according to the conventional method gave peaks ascribed to mannose, fucose and galactose which were not completely separated, but the peaks ascribed to fucose and galactose, in particular, were found overwrapped with each other (FIG. 2-2). From these results, it was shown that the novel method is superior to the conventional one as a method for analysis of neutral sugars, especially as a method for quantitative analysis.

[Analysis of M6P Standard Solution]

Figure 31:
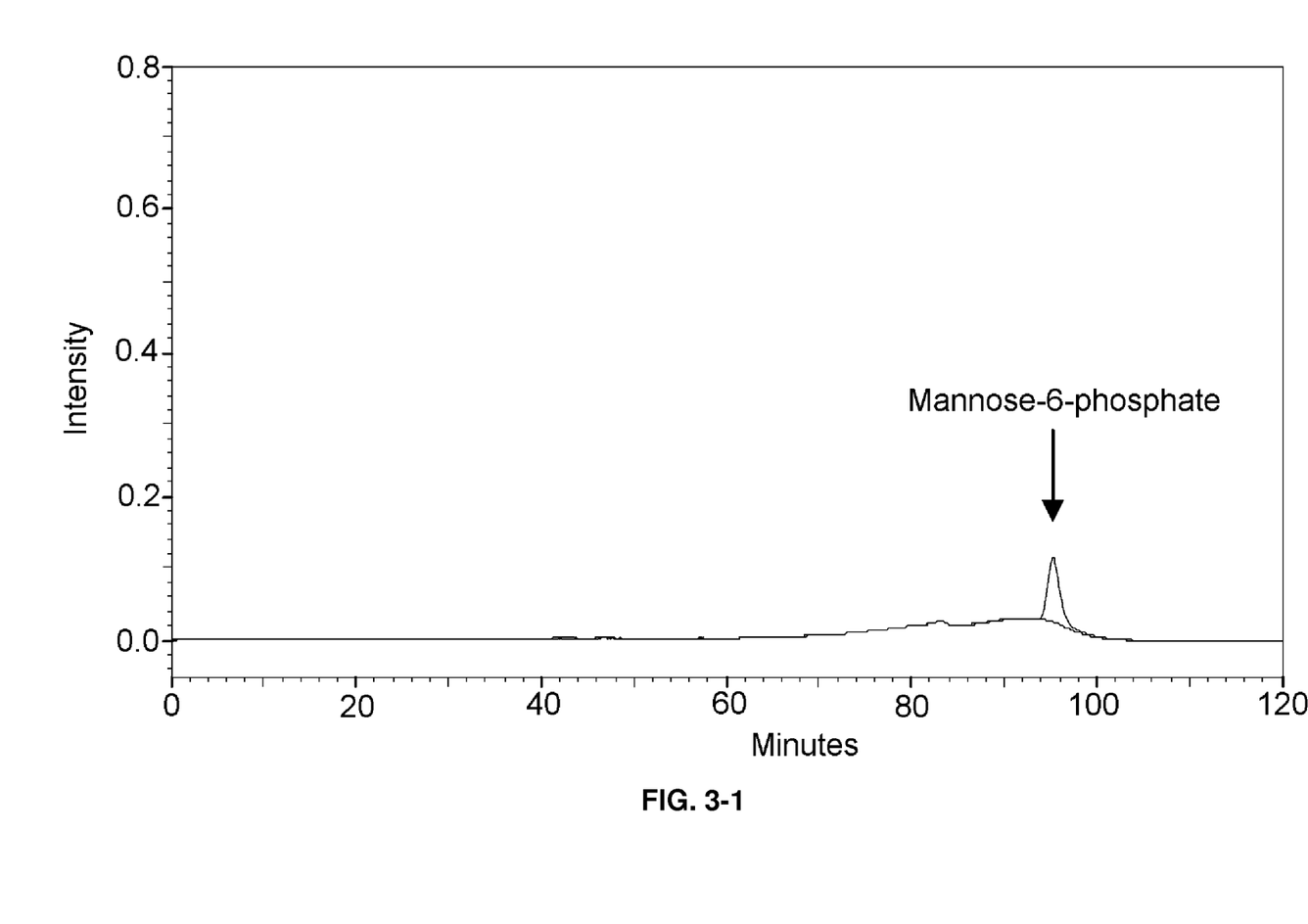
Figure 32:
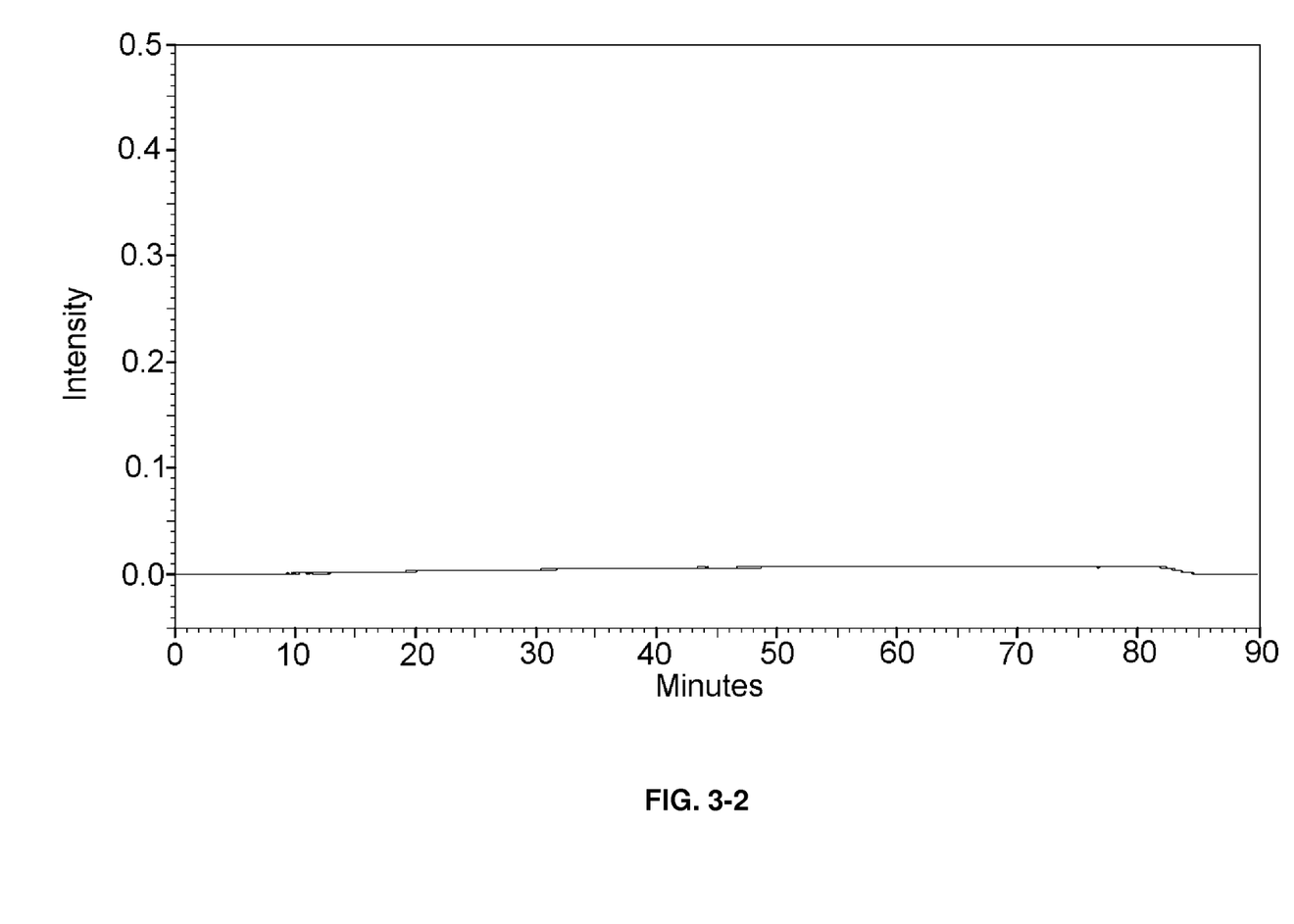

Analysis of the M6P standard solution according to the novel method gave a peak ascribed to M6P (FIG. 3-1). On the other hand, analysis of the M6P standard solution according to the conventional method gave no peak ascribed to M6P (FIG. 3-2). These results are thought to be due to the addition of sodium chloride to the mobile phase acting, while enabling simultaneous analysis of other reducing sugars, to modulate the retention power of the anion exchanger resin so that the retention power toward M6P is reduced, which in the conventional method remained bound to the anion exchanger resin and resisted easy elution. In the above examples of the novel method, M6P was not eluted along with the neutral sugars during the 10 min period when the concentration of sodium chloride in the mobile phase was once increased to 200 mM, but was eluted after the concentration of sodium chloride was decreased to 20 mM. However, it is evident that M6P must be eluted if the mobile phase is kept to flow without decreasing the concentration of sodium chloride from 200 mM, for it is clear from the whole results of the examples that the higher the concentration of sodium chloride is, the easier becomes elution of M6P.

[Mixture Solution of Neutral Sugars Mixture Standard Solution and M6P Standard Solution]

Figure 41:
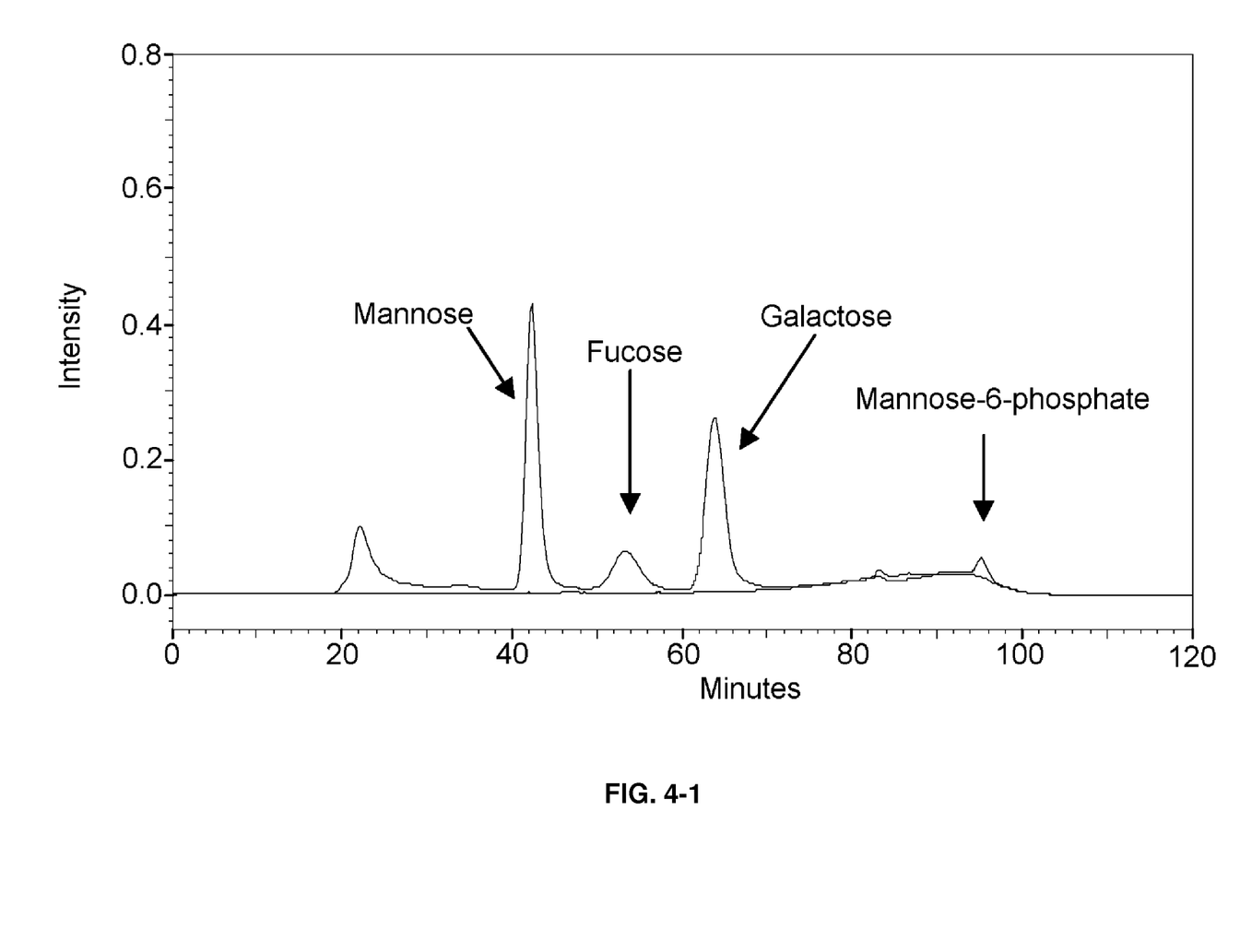
Figure 42:
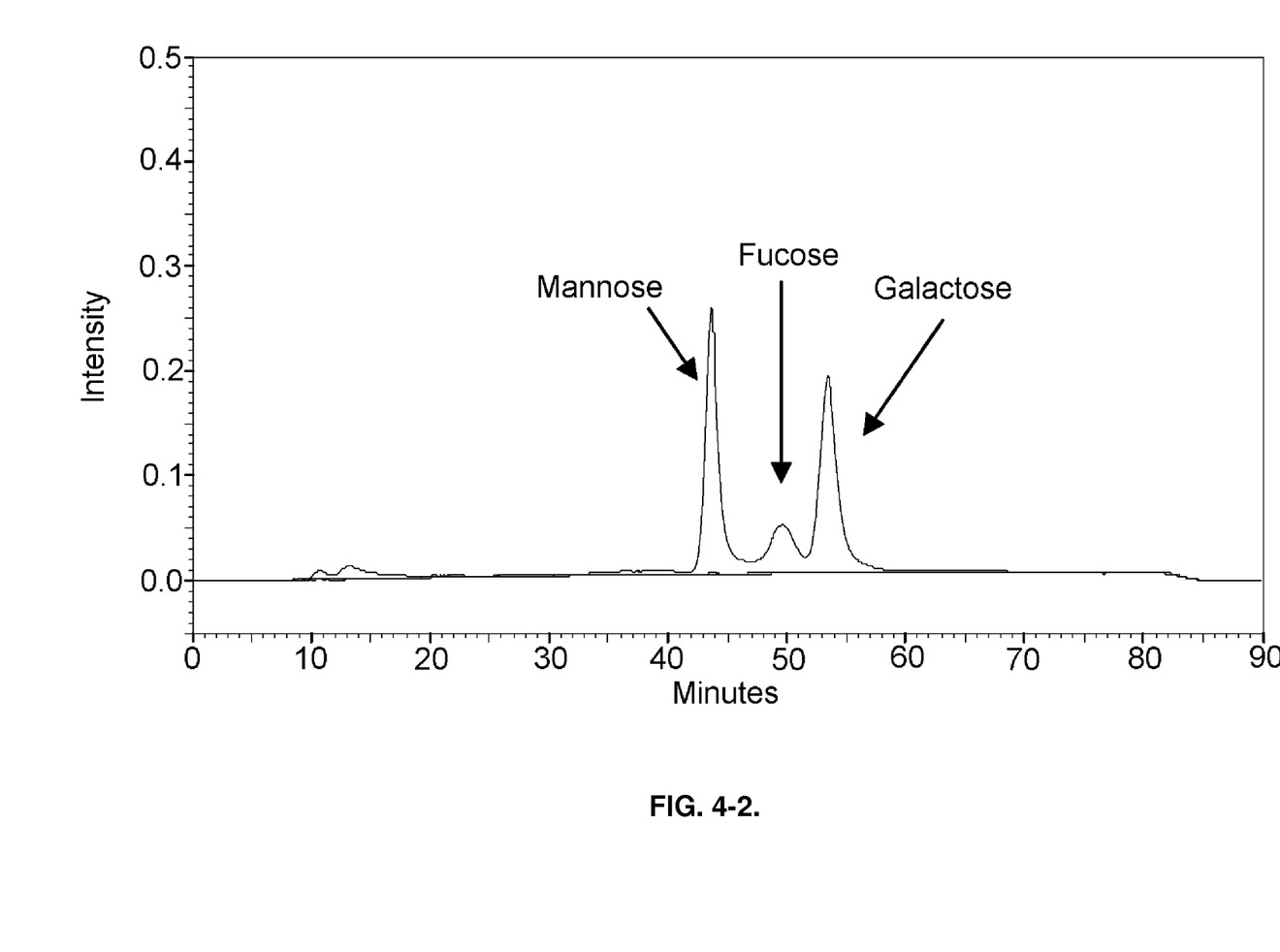

Analysis of the mixture solution of the neutral sugars mixture standard solution and M6P standard solution according to the novel method gave completely separated peaks ascribed to mannose, fucose, galactose and M6P (FIG. 4-1). On the other hand, analysis of the mixture solution of the neutral sugars mixture standard solution and M6P standard solution according to the conventional method gave peaks ascribed to mannose, fucose and galactose which were not completely separated, and no peak ascribed to M6P was obtained (FIG. 4-2). These results indicated that the novel method is strikingly superior to the conventional method as a method for analysis of neutral sugars such as mannose, fucose, and galactose, and further as a method for analysis of M6P, especially as a method for quantitative analysis for them. Further, it was shown that as the novel method allows simultaneous analysis of M6P and mannose, the method makes it possible to assess the stability of M6P, a component of sugar chains and glycoproteins, by determining the amount of mannose that could be generated by decomposition of M6P.

INDUSTRIAL APPLICABILITY

In post-column fluorometric determination-boric acid complex anion exchanger method, the present invention can be used as a novel method for analysis of reducing sugars which enables analysis of M6P, improves resolution between neutral sugars, and further, eliminates the problem of clogging of the tubing which accompanies the former method.

| [Explanation of Signs] |
| --- |
| 1: Autosampler |
| 2: Column oven |
| 3: Column |
| 4: Heat block |
| 5: Fluorescence detector |
| A: Solution A (A') |
| B: Solution B (B') |
| C: Reagent solution for reaction |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding Japanese application No. P2009-060917, filed Mar. 13, 2009, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid comprising at least a predetermined concentration of a water-soluble inorganic salt through the column;

supplying to the column continuously at a predetermined flow rate a second mobile phase comprising the salt at an elevated concentration compared with the first mobile phase to eluate reducing sugars;

leading the eluate from the column continuously to a flow path;

continuously adding at least one basic amino acid at a predetermined rate to the eluate at a predetermined position of the flow path to make a mixture solution which continuously flows through the flow path;

heating the mixture solution by letting the mixture solution flow through a heating zone at a predetermined temperature of the flow path over a predetermined length of time; and continuously measuring and recording the intensity of fluorescent light emitted from the mixture solution while continuously irradiating the mixture solution thus heated and flowing through the flow path with excitation light at a predetermined position of the flow path;

wherein, in the first mobile phase, the concentration of boric acid is 50-150 mM and the concentration of the water-soluble inorganic salt is 10-30 mM.

2. The method for separation analysis according to claim 1, wherein the concentration of boric acid in the first and the second mobile phases is 75-125 mM.

3. The method for separation analysis according to claim 1, wherein separation of reducing sugars is performed with the column heated at a temperature not exceeding 70° C.

4. The method for separation analysis according to claim 1, wherein the basic amino acid is added so that the concentration thereof reaches 0.1-2 w/v % in the mixture solution.

5. The method for separation analysis according to claim 1, wherein the basic amino acid is selected from the group consisting of arginine, lysine and histidine.

6. The method for separation analysis according to claim 1, wherein the temperature of the heating zone at a predetermined temperature is 140-180° C.

7. The method for separation analysis according to claim 1, wherein the concentration of the salt in the second mobile phase is increased at least up to 200 mM.

8. The method for separation analysis according to claim 1, wherein the reducing sugars include neutral sugars.

9. The method for separation analysis according to claim 1, wherein the reducing sugars include mannose, glucose or fucose.

10. A method for separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid comprising at least a predetermined concentration of a water-soluble inorganic salt through the column;

supplying to the column continuously at a predetermined flow rate a second mobile phase comprising the salt at an elevated concentration compared with the first mobile phase to eluate reducing sugars;

leading the eluate from the column continuously to a flow path;

continuously adding at least one basic amino acid at a predetermined rate to the eluate at a predetermined position of the flow path to make a mixture solution which continuously flows through the flow path;

heating the mixture solution by letting the mixture solution flow through a heating zone at a predetermined temperature of the flow path over a predetermined length of time; and continuously measuring and recording the intensity of fluorescent light emitted from the mixture solution while continuously irradiating the mixture solution thus heated and flowing through the flow path with excitation light at a predetermined position of the flow path;

wherein the pH of the first and the second mobile phases is 7.5-9.5.

11. A method for separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid containing at least a predetermined concentration of a water-soluble inorganic salt through the column;

supplying to the column continuously at a predetermined flow rate a second mobile phase containing the salt at an elevated concentration compared with the first mobile phase to eluate reducing sugars;

leading the eluate from the column continuously to a flow path;

continuously adding at least one basic amino acid at a predetermined rate to the eluate at a predetermined position of the flow path to make a mixture solution which continuously flows through the flow path;

heating the mixture solution by letting the mixture solution flow through a heating zone at a predetermined temperature of the flow path over a predetermined length of time; and continuously measuring and recording the intensity of fluorescent light emitted from the mixture solution while continuously irradiating the mixture solution thus heated and flowing through the flow path with excitation light at a predetermined position of the flow path, wherein the water-soluble inorganic salt is sodium chloride.

12. A method for separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid containing at least a predetermined concentration of a water-soluble inorganic salt through the column;

supplying to the column continuously at a predetermined flow rate a second mobile phase containing the salt at an elevated concentration compared with the first mobile phase to eluate reducing sugars;

leading the eluate from the column continuously to a flow path;

continuously adding at least one basic amino acid at a predetermined rate to the eluate at a predetermined position of the flow path to make a mixture solution which continuously flows through the flow path;

heating the mixture solution by letting the mixture solution flow through a heating zone at a predetermined temperature of the flow path over a predetermined length of time; and continuously measuring and recording the intensity of fluorescent light emitted from the mixture solution while continuously irradiating the mixture solution thus heated and flowing through the flow path with excitation light at a predetermined position of the flow path;

wherein the reducing sugars include mannose-6-phosphate.

13. An aqueous solution for use as the first mobile phase in a separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid containing at least a predetermined concentration of a water-soluble inorganic salt through the column;

supplying to the column continuously at a predetermined flow rate a second mobile phase containing the salt at an elevated concentration compared with the first mobile phase to eluate reducing sugars;

leading the eluate from the column continuously to a flow path;

continuously adding at least one basic amino acid at a predetermined rate to the eluate at a predetermined position of the flow path to make a mixture solution which continuously flows through the flow path;

heating the mixture solution by letting the mixture solution flow through a heating zone at a predetermined temperature of the flow path over a predetermined length of time; and continuously measuring and recording the intensity of fluorescent light emitted from the mixture solution while continuously irradiating the mixture solution thus heated and flowing through the flow path with excitation light at a predetermined position of the flow path;

and wherein the aqueous solution for use as the first mobile phase contains 50-150 mM boric acid and 10-30 mM sodium chloride.

14. A solid composition for use to prepare the aqueous solution of claim 13 by dissolving the same in water, wherein the solid composition comprises boric acid and sodium chloride at a molar ratio of 1:0.1 to 1:0.5.

15. An aqueous solution for use to prepare the second mobile phase by mixing with the first mobile phase in a method for separation analysis of reducing sugars contained in a sample by column chromatography, comprising loading the sample on an anion exchanger resin column, and washing the column by allowing a sufficient volume of a first mobile phase to flow consisting of an aqueous solution of a predetermined concentration of boric acid comprising at least a predetermined concentration of a water-soluble inorganic salt through the column;

supplying to the column continuously at a predetermined flow rate a second mobile phase comprising the salt at an elevated concentration compared with the first mobile phase to eluate reducing sugars;

leading the eluate from the column continuously to a flow path;

continuously adding at least one basic amino acid at a predetermined rate to the eluate at a predetermined position of the flow path to make a mixture solution which continuously flows through the flow path;

heating the mixture solution by letting the mixture solution flow through a heating zone at a predetermined temperature of the flow path over a predetermined length of time; and continuously measuring and recording the intensity of fluorescent light emitted from the mixture solution while continuously irradiating the mixture solution thus heated and flowing through the flow path with excitation light at a predetermined position of the flow path;

and wherein the aqueous solution for use to prepare the second mobile phase contains 50-150 mM boric acid and 200-250 mM sodium chloride.

16. A solid composition for use to prepare the aqueous solution of claim 15 by dissolving the same in water, wherein the solid composition comprises boric acid and sodium chloride at a molar ratio of 1:1.5 to 1:2.5.

* * * * *